(12) United States Patent
Allen et al.

(10) Patent No.: US 9,493,415 B2
(45) Date of Patent: Nov. 15, 2016

(54) PROCESS FOR FLUORINATING COMPOUNDS

(71) Applicants: Dow AgroSciences LLC, Indianapolis, IN (US); University of Michigan, Ann Arbor, MI (US)

(72) Inventors: Laura Allen, Ypsilanti, MI (US); Melanie Sanford, Ann Arbor, MI (US); Shin Hee Lee, Ann Arbor, MI (US); Douglas Bland, Mason, OH (US); Yang Cheng, Midland, MI (US); Gary Roth, Midland, MI (US); Joseck M. Muhuhi, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/539,696

(22) Filed: Nov. 12, 2014

(65) Prior Publication Data

US 2015/0141654 A1    May 21, 2015

Related U.S. Application Data

(60) Provisional application No. 61/902,989, filed on Nov. 12, 2013.

(51) Int. Cl.
*C07D 213/803* (2006.01)

(52) U.S. Cl.
CPC ................. *C07D 213/803* (2013.01)

(58) Field of Classification Search
None
See application file for complete search history.

(56) References Cited

U.S. PATENT DOCUMENTS

| | | |
|---|---|---|
| 7,592,486 B2 | 9/2009 | DiMagno et al. |
| 7,939,697 B2 | 5/2011 | Hagiya |
| 2004/0144947 A1 | 7/2004 | Garayt et al. |
| 2006/0009643 A1 | 1/2006 | Pleschke et al. |
| 2012/0190857 A1 | 7/2012 | Arndt et al. |
| 2012/0190858 A1 | 7/2012 | Zhu et al. |
| 2012/0190859 A1 | 7/2012 | Zhu et al. |
| 2012/0190860 A1 | 7/2012 | Whiteker et al. |
| 2014/0031556 A1 | 1/2014 | Renga et al. |
| 2014/0031558 A1 | 1/2014 | Renga et al. |
| 2014/0171650 A1 | 6/2014 | Giampietro et al. |
| 2014/0171653 A1 | 6/2014 | Renga et al. |
| 2014/0171654 A1 | 6/2014 | Johnson et al. |
| 2014/0206881 A1 | 7/2014 | Zhu et al. |
| 2014/0296533 A1 | 10/2014 | Renga et al. |
| 2015/0133672 A1 | 5/2015 | Allen et al. |
| 2015/0133673 A1 | 5/2015 | Sanford et al. |

FOREIGN PATENT DOCUMENTS

| | | |
|---|---|---|
| EP | 0146924 A2 | 12/1984 |
| EP | 1698606 A1 | 9/2006 |
| WO | 02092608 A2 | 11/2002 |
| WO | 03076366 A2 | 9/2003 |
| WO | 03106379 A1 | 12/2003 |
| WO | 2004048350 A2 | 6/2004 |
| WO | 2006055748 A2 | 5/2006 |
| WO | 2012163905 A1 | 12/2012 |

OTHER PUBLICATIONS

Liang et al., 52 Ang. Chem. Int. Ed. 8214-8264 (2013).*
International Search Report and Written Opinion for PCT/US2014/065212 dated Mar. 31, 2015.
Anbarasan et al., Efficeient Synthesis of Aryl Fluorides, Angew. Chem., Int. Ed., 49:2219-2222, 2010.
Balz et al., On aromatic fluorine compounds, I.: A new process for their preparation. Ber. Deutsch. Chem. Ges., 60:1186, 1927.
Barnette et al., N-Fluoro-N-alkylsulfonamides: Useful Reagents for the Fluorination of Carbanions, J. Am. Chem. Soc., 106:452-454, 1984.
Cox et al., "Anhydrous" Tetrabutylammonium Fluoride: A Mild but Highly Efficient Source of Nucleophilic Fluoride Ion, J. Org. Chem., 49:3216-3219, 1984.
Differding et al., Nucleophilic Substitution Versus Electron Transfer: 2.SH1 at Fluorine and Electron Transfer are Competing and Different Pathways in Electrophilic Fluorinations, Tetrahedron Lett., 32:3819-3822, 1991.
Heinz et al., A simple synthesis of tetraalkylammonium salts with functional anions. Justis Liebig Annalen der Chemie, 12:1937, 1978.
Higgins et al., PKas of the conjugate acids of N-heterocyclic carbenes in water, Chem. Commun., 47:1559-1561, 2011.
Kim et al., New Method of Fluorination Using Potassium Fluoride in Ionic Liquid: Significantly Enhanced Reactivity of Fluoride and Improved Selectivity, J. Am. Chem. Soc.. 124:10278-10279, 2002.
Liang et al., Introduction of Fluorine and Fluorine-Containing Functional Groups, Angewandte Chemie International Edition, 52:8214-8264, 2013.
Okamoto et al., Activity and behavior of imidazolium salts as a phase transfer catalyst for a liquid-liquid phase system, Tetrahedron Letters, 47:8055-8058, 2006.
Sharma et al., Instability of Anhydrous Tetra-N-alkylammonium Fluorides, J. Org. Chem., 48:2112-2114, 1983.
Sun et al., Anhydrous Tetrabutylammonium Fluoride, J. Am. Chem. Soc., 127:2050-2051, 2005.
Sun et al., Room-Temperature Nucleophilic Aromatic Fluorination: Experimental and Theoretical Studies, Angewandte Chemie International Edition, 45:2720-2725, 2006.
Walsh et al., Mutations in an Auxin Receptor Homolog AFB5 and in SGT1b Confer Resistance to Synthetic Picolinate Auxins and Not to 2,4-Dichlorophenoxyacetic Acid or Indole-3-Acetic Acid in Arabidopsis, Plant Physiology, 142:542-552, 2006.
Yamada et al., Convenient Electrophilic Fluorination of Functionalized Aryl and Heteroaryl Magnesium Reagents, Angew. Chem., Int. Ed., 49:2215-2218, 2010.
Zhong et al., Direct Formation of 2,3,5-Trichloropyridine and its Nucleophilic Displacement Reactions in Ionic Liquid. Synthetic Commun. 34(23):4301-4311, 2004.

(Continued)

*Primary Examiner* — Timothy R Rozof
(74) *Attorney, Agent, or Firm* — Michael R. Asam; Meunier Carlin & Curfman, LLC

(57) ABSTRACT

Methods of preparing a fluorinated substrate by combining potassium fluoride, a quaternary ammonium salt, and a substrate substituted with at least one chloro, bromo, sulfonyl, or nitro group to thereby provide the fluorinated substrate are disclosed.

20 Claims, 8 Drawing Sheets

(56) References Cited

OTHER PUBLICATIONS

Office Action from United States Patent Office for U.S. Appl. No. 14/529,700, dated Mar. 17, 2015.
International Search Report and Written Opinion for PCT/US2014/065272, dated Jan. 30, 2015.
International Search Report and Written Opinion for PCT/US2014/065199, dated Jan. 30, 2015.
Bobbio et al., Removal of Fluorine from and Introduction of Flourine into Polyhalopyridines: An Exercise in Nucleophilic Hetarenic Substitution. Eur. J. Chem. 11(6):1903-1910, 2005.
Allen et al., Mild Fluorination of Chloropyridines with in situ Generated Anhydrous Tetrabutylammonium Fluoride. J. Org. Chem. 17(12):5827-5833, 2014.
Allen et al., Developing Efficient Nucleophilic Fluorination Methods and Application to Substituted Picolinate Esters. Org. Proc. Res. Dev. 18(8):1045-1054, 2014.
Sagar et al., Synthetic studies towards the antiviral pyrazine derivative T-205. Proceedings of the 13th Electronic Conference on Synthetic Organic Chemistry Nov. 1-30, 2009, 13:1-3.
Maggini et al., A general procedure for the fluorodenitration of aromatic substrates. J. Org. Chem. 56(22):6406-6411, 1991.
Sasson et al., Tetramethylammonium chloride as a selective and robust phase transfer catalyst in solid-liquid halex reaction: the role of water. Chem. Commun. 197-298, 1996.
Notice of Allowance U.S. Appl. No. 14/539,700, dated Aug. 19, 2015.

* cited by examiner

PROCESS FOR FLUORINATING COMPOUNDS

CROSS REFERENCE TO RELATED APPLICATIONS

This application claims the benefit of U.S. Provisional Patent Application Ser. No. 61/902,989 filed Nov. 12, 2013, the entire disclosure of which is expressly incorporated herein by reference.

FIELD

This application relates generally to methods of fluorinating compounds and to fluorinated compounds.

BACKGROUND

Fluorinated organic molecules are increasingly used in life science industries. The presence of a fluorine substituent can have positive effects on the biological properties of compounds. Thus, synthetic techniques for fluorinating compounds are a significant area of interest.

The selective fluorination of aryl and heteroaryl substrates is a challenging synthetic problem. As an example, mono- and di-chloro substituted picolinate esters are difficult to fluorinate and require more expensive metal fluorides (e.g., cesium fluoride (CsF)) to generate acceptable yields. Under Halex (halogen exchange) conditions, which use potassium fluoride, the chemical yields are often quite low (<20%). Also, Halex conditions usually require a phase transfer catalyst, a high boiling solvent, and high temperatures. Such conditions can preclude the use of Halex conditions in many systems. What is needed are new methods for fluorinating compounds, especially a wide variety of fluorinated compounds, and the methods and compounds disclosed herein address these and other needs.

SUMMARY

The subject matter disclosed herein relates to methods of making compositions and the compositions themselves. In particular, the subject matter disclosed herein generally relates to methods of fluorinating compounds and to fluorinated compounds. In certain specific aspects, disclosed herein are methods of preparing a fluorinated substrate that comprise combining potassium fluoride, one or more quaternary ammonium salts, and a substrate substituted with at least one chloro, bromo, sulfonyl, or nitro group, to thereby provide the fluorinated substrate. In the disclosed methods, the potassium fluoride, quaternary ammonium salt, and/or substrate can be combined in the presence of a solvent.

The disclosed methods are particularly well suited for fluorinating heteroaryl substrates having Formula IA or IB:

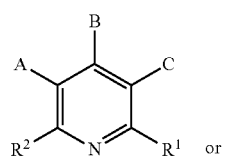

IA

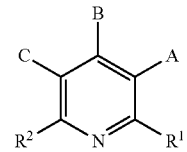

IB wherein A is Cl, Br, $SO_2R^3$, or $NO_2$; B is H, Cl, Br, $SO_2R^3$, or $NO_2$; C is H, Cl, Br, $SO_2R^3$, or $NO_2$; $R^1$ is H, CN, or $CO_2R^3$, wherein each $R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and $R^2$ is H, substituted or unsubstituted aryl, substituted or unsubstituted heteroaryl. Such substrates are particularly difficult to fluorinate. One of the resulting products of the disclosed methods upon substrates having Formula IA or IB are compounds having Formula IIA or IIB

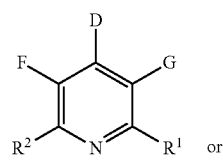

IIA or

IIB

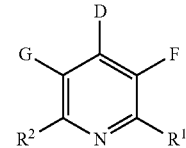

wherein D is B, as is defined above, or F; and G is B, as is defined above, or F.

The disclosed products represented by Formula IIA or IIB are often obtained in greater yields than the difluorinated or para-fluorinated product, indicating the fluorinating process disclosed herein is relatively selective.

Various quaternary ammonium salts can be used in the disclosed methods, such as those comprising a quaternary ammonium cation having the formula) $^+N(R^{20})(R^{21})(R^{22})(R^{23})$, wherein $R^{20}$-$R^{23}$ are, independent of one another, substituted or unsubstituted $C_1$-$C_{40}$ alkyl, substituted or unsubstituted $C_2$-$C_{40}$ alkenyl, substituted or unsubstituted $C_2$-$C_{40}$ alkynyl, substituted or unsubstituted $C_3$-$C_8$ cycloalkyl, substituted or unsubstituted $C_3$-$C_8$ cycloalkenyl, or substituted or unsubstituted aryl. In certain examples disclosed herein, $R^{20}$-$R^{23}$ can be methyl, ethyl, propyl, butyl, pentyl, or hexyl. In still other examples, the quaternary ammonium salt can comprise a trialkylbenzylammonium cation having Formula III:

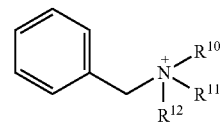

III wherein $R^{10}$-$R^{12}$ are, independent of one another, substituted or unsubstituted $C_1$-$C_{40}$ alkyl or substituted or unsubstituted $C_3$-$C_8$ cycloalkyl. In certain examples, $R^{10}$ can be $C_{10}$-$C_{40}$ alkyl and $R^{11}$ and $R^{12}$ are substituted or unsubstituted $C_1$-$C_6$ alkyl.

In other aspects, the subject matter disclosed herein relates to methods of preparing a fluorinated heteroaryl substrate that comprise mixing potassium fluoride, a quaternary ammonium salt, a solvent, and a heteroaryl substrate having Formula IA or IB wherein A in the Formula IA or IB is Cl, Br, $SO_2R^3$, or $NO_2$; B is H, Cl, Br, $SO_2R^3$, or $NO_2$; C is H, Cl, Br, $SO_2R^3$, or $NO_2$; $R^1$ is H, CN, or $CO_2R^3$, wherein each $R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and $R^2$ is H, substituted or unsubstituted aryl, substituted or unsubstituted heteroaryl.

In still other aspects, the subject matter disclosed herein relates to products prepared by the methods disclosed herein. In still other aspects, the subject matter disclosed herein relates to fluorinated compounds, such as those prepared by the disclosed methods.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
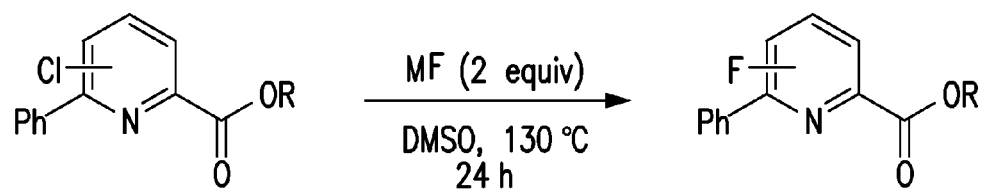
FIG. 1 contains a graph showing fluorination yield of the reaction depicted above the graph (percent (%)) with model substrates, isopropyl 5-chloro-6-phenylpicolinate (DS-2) or ethyl 5-chloro-6-phenylpicolinate (DS-1), with cesium fluoride (CsF) or potassium fluoride (KF).
Figure 1:
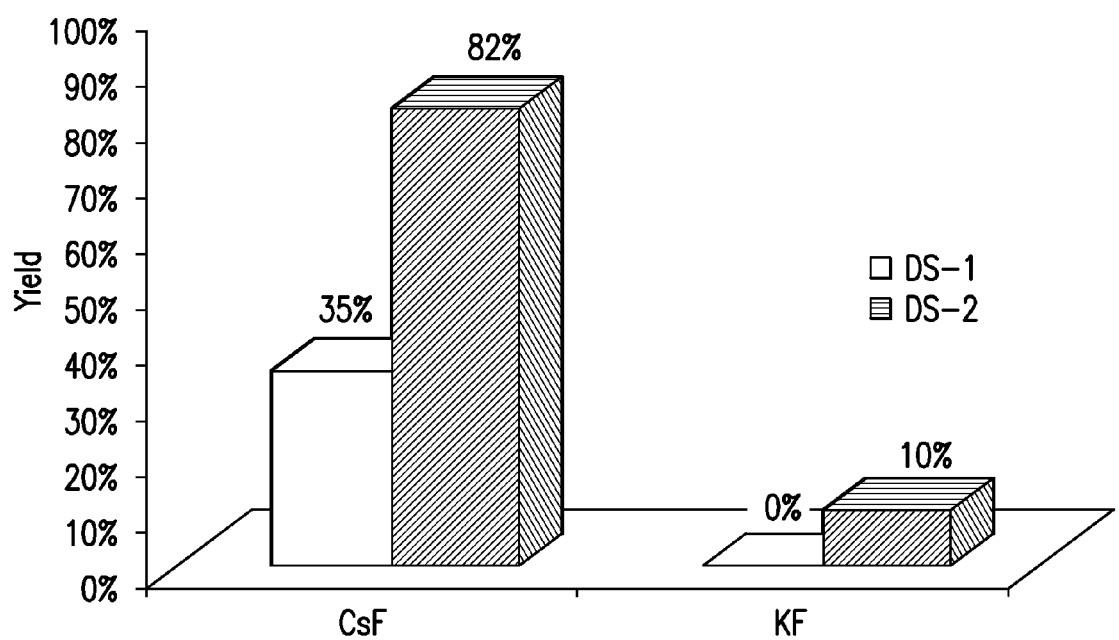

The materials, compounds, compositions, articles, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence upon which the reference is relied.

GENERAL DEFINITIONS

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes a mixture of two or more such agents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ wherein $Z^1$ is alkyl as defined above.

The term "alkenyl" as used herein is a hydrocarbon group of from 2 to 24 carbon atoms with a structural formula containing at least one carbon-carbon double bond. Asymmetric structures such as ($Z^1Z^2$)C=C($Z^3Z^4$) are intended to include both the E- and Z-isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above wherein at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. In certain specific examples cycloalkyl is a $C_{3-8}$ cycloalkyl.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," wherein at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a shorthand notation for C=O, which is also referred to herein as a "carbonyl."

The terms "amine" or "amino" as used herein are represented by the formula —$NZ^1Z^2$, wherein $Z^1$ and $Z^2$ can each be a substituent group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)$NZ^1Z^2$.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)$Z^1$ or —C(O)O$Z^1$, wherein $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, wherein $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, wherein $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to fluorine, chlorine, bromine, and iodine. The corresponding term "halo", e.g., fluoro, chloro, bromo, and iodo as used herein refer to the corresponding radical or ion.

The term "hydroxyl" as used herein is represented by the formula —OH.

The term "cyano" as used herein is represented by the formula —CN. Cyanide is used to refer to the cyanide ion CN$^-$.

The term "nitro" as used herein is represented by the formula —$NO_2$.

The term "silyl" as used herein is represented by the formula —$SiZ^1Z^2Z^3$, wherein $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —$S(O)_2Z^1$, wherein $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

The term "thiol" as used herein is represented by the formula —SH.

The term "thio" as used herein is represented by the formula —S—.

"$R^1$," "$R^2$," "$R^3$," "Re," etc., wherein n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Methods

Disclosed herein are methods of fluorinating substrates that use particular quaternary ammonium salts in conjunction with potassium fluoride (KF) to generate the desired fluorination product in yields often similar or better than the CsF control. The disclosed methods comprise combining KF, one or more quaternary ammonium salts, and a substrate substituted with at least one chloro, bromo, sulfonyl, or nitro group, to thereby provide the fluorinated substrate.

In the disclosed methods, the KF and substrate can be combined, followed by the addition of the quaternary ammonium salt. Alternatively, the quaternary ammonium salt and substrate can be combined, followed by the addition of KF. In another alternative, the KF, substrate, and quaternary ammonium salt can be combined simultaneously. The combination of these materials can be accomplished by methods known in the art. For example, the KF can be added to the substrate, or vice versa. Typically, the addition can be accompanied by mixing, stirring, shaking or other form of agitation. Alternatively, the quaternary ammonium salt can be added to the substrate, or vice versa. Again this addition can be accompanied by mixing, stirring, shaking or other form of agitation. In still another example, the quaternary ammonium salt can be added to the KF, or vice versa, which can be accompanied by mixing, stirring, shaking or other form of agitation.

Further, the combination of these materials can be conducted at elevated temperature, e.g., from about 30° C. to about 225° C., from about 50° C. to about 200° C., from about 100° C. to about 150° C., from about 100° C. to about 225° C., from about 150° C. to about 225° C., from about 30° C. to about 100° C., from about 50° C. to about 100° C., from about 30° C. to about 50° C., or from about 75° C. to about 200° C. In certain examples, the materials can be combined at room temperature.

Still further, once combined, the resulting combination of KF, substrate, quaternary ammonium salt, and optional solvent, can be heated. The amount of heat can be adjusted depending on the substrate and progress of the reaction, which can be monitored by methods known in the art. In general, the combination can be heated to from about 50 to about 250° C., from about 75° C. to about 225° C., from about 100° C. to about 200° C., from about 125° C. to about 175° C., from about 50° C. to about 150° C., from about 75° C. to about 125° C., from about 150° C. to about 250° C., or from about 100° C. to about 150° C.

The amount of KF can vary depending on the particular substrate. In certain examples, from about 0.5 to about 10 equivalents of KF can be used per equivalent of the substrate. For example, from about 0.5 to about 9 equivalents, from about 0.5 to about 8 equivalents, from about 0.5 to about 7 equivalents, from about 0.5 to about 6 equivalents, from about 0.5 to about 5 equivalents, from about 0.5 to about 4 equivalents, from about 0.5 to about 3 equivalents, from about 0.5 to about 2 equivalents, from about 1 to about 10 equivalents, from about 1 to about 9 equivalents, from about 1 to about 8 equivalents, from about 1 to about 7 equivalents, from about 1 to about 6 equivalents, from about 1 to about 5 equivalents, from about 1 to about 4 equivalents, from about 1 to about 3 equivalents, from about 2 to about 10 equivalents, from about 2 to about 9 equivalents, from about 2 to about 8 equivalents, from about 2 to about 7 equivalents, from about 2 to about 6 equivalents, from about 2 to about 5 equivalents, from about 2 to about 4 equivalents, from about 2 to about 3 equivalents, from about 3 to about 10 equivalents, from about 3 to about 9 equivalents, from about 3 to about 8 equivalents, from about 3 to about 7 equivalents, from about 3 to about 6 equivalents, from about 3 to about 5 equivalents, from about 3 to about 4 equivalents, from about 4 to about 10 equivalents, from about 4 to about 9 equivalents, from about 4 to about 8 equivalents, from about 4 to about 7 equivalents, from about 4 to about 6 equivalents, from about 4 to about 5 equivalents, from about 5 to about 10 equivalents, from about 5 to about 9 equivalents, from about 5 to about 8 equivalents, from about 5 to about 7 equivalents, from about 5 to about 6 equivalents, from about 6 to about 10 equivalents, from about 6 to about 9 equivalents, from about 6 to about 8 equivalents, from about 6 to about 7 equivalents, from about 7 to about 10 equivalents, from about 7 to about 9 equivalents, from about 7 to about 8 equivalents, from about 8 to about 10 equivalents, from about 8 to about 9 equivalents, from about 9 to about 10 equivalents, or from about 0.5 to about 1 equivalent of KF can be used per equivalent of the substrate.

Quaternary Ammonium Salts

In the disclosed methods, various quaternary ammonium salts can be used. In certain examples, the quaternary ammonium salt can comprise an tetraalkyl ammonium cation having Formula $^+N(R^{20})(R^{21})(R^{22})(R^{23})$, wherein $R^{20}$-$R^{23}$ are, independent of one another, substituted or unsubstituted $C_1$-$C_{40}$ alkyl, substituted or unsubstituted $C_2$-$C_{40}$ alkenyl, substituted or unsubstituted $C_2$-$C_{40}$ alkynyl, substituted or unsubstituted $C_3$-$C_8$ cycloalkyl, or substituted or unsubstituted $C_3$-$C_8$ cycloalkenyl. In specific examples, each $R^{20}$-$R^{23}$ can be, independent of one another, substituted or unsubstituted $C_1$-$C_6$ alkyl or substituted or unsubstituted $C_3$-$C_8$ cycloalkyl. In other examples, each $R^{20}$-$R^{23}$ can be, independent of one another, methyl, ethyl, propyl, isopropyl, butyl, sec-butyl, isobutyl, pentyl, isopentyl, hexyl, 2-ethylbutyl, or 2-methylpentyl. In specific examples, the tetraalkyl ammonium cation can be a di-dodecyl dimethyl ammonium, di-tetradecyl dimethyl ammonium, dihexadecyl dimethyl ammonium, cetyl trimethyl ammonium, lauryl trimethyl ammonium, myristyl trimethyl ammonium, stearyl trimethyl ammonium, arachidyl trimethyl ammonium, cetyl dimethylethyl ammonium, lauryl dimethylethyl ammonium, myristyl dimethylethyl ammonium, stearyl dimethylethyl ammonium, or arachidyl dimethylethyl ammonium, or mixtures thereof. In other examples, the tetraalkyl ammonium cation is tetrabutylammonium, tetrapropylammonium, tetraethylammonium, or tetramethylammonium.

In further examples, the quaternary ammonium salt can comprise a trialkyl benzylammonium cation having Formula III:

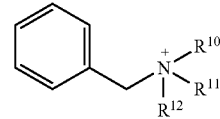

wherein $R^{10}$-$R^{12}$ are, independent of one another, substituted or unsubstituted $C_1$-$C_{40}$ alkyl, substituted or unsubstituted $C_2$-$C_{40}$ alkenyl, substituted or unsubstituted $C_2$-$C_{40}$ alkynyl, substituted or unsubstituted $C_3$-$C_8$ cycloalkyl, substituted or unsubstituted $C_3$-$C_8$ cycloalkenyl. In other examples each $R^{10}$-$R^{12}$ can be, independent of one another, substituted or unsubstituted $C_1$-$C_{40}$ alkyl or substituted or unsubstituted $C_3$-$C_8$ cycloalkyl. In other examples each $R^{10}$-$R^{12}$ can be, independent of one another, substituted or unsubstituted $C_1$-$C_{18}$ alkyl.

In still other examples, trialkyl benzylammonium cations of Formula III can have $R^{10}$ as a long chain alkyl group (i.e., $C_{11}$-$C_{40}$) and $R^{11}$ and $R^{12}$ as short chain alkyl groups (i.e., $C_1$-$C_{10}$). For example, $R^{10}$ in Formula III can be a dodecyl (lauryl), tetradecyl (myristyl), hexadecyl (palmityl or cetyl), octadecyl (stearyl), or eicosyl (arachidyl) group, and $R^{11}$-$R^{12}$ can each be, independent of one another, a methyl, ethyl, propyl, butyl, pentyl, hexyl, heptyl, octyl, nonyl, or decyl group. In specific examples, the trialkyl benzylammonium cation can be, cetyl dimethyl benzyl ammonium, lauryl dimethyl benzyl ammonium, myristyl dimethyl benzyl ammonium, stearyl dimethyl benzyl ammonium, arachidyl dimethyl benzyl ammonium, cetyl methylethyl benzyl ammonium, lauryl methylethyl benzyl ammonium, myristyl methylethyl benzyl ammonium, stearyl methylethyl benzyl ammonium, or arachidyl methylethyl benzyl ammonium.

The quaternary ammonium salt can have various anions in combination with the ammonium cation. For example, the quaternary ammonium salt can have an anion chosen from $Cl^-$, $Br^-$, and $C_1$-$C_6CO_2^-$. Other suitable anions include, but are not limited to, $OH^-$, $I^-$, $CN^-$, $SCN^-$, $OCN^-$, $CNO^-$, $N_3^-$, $CO_3^{2-}$, $HCO_3^-$, $HS^-$, $NO_2^-$, $NO_3^-$, $SO_4^{2-}$, $PO_4^{3-}$, $PF_6^-$, $ClO^-$, $ClO_2^-$, $ClO_3^-$, $ClO_4^-$, $CF_3CO_2^-$, $CF_3SO_3^-$, $BF_4^-$, and $C_6H_5CO_2^-$. In specific examples, the quaternary ammonium salt comprises one or more $C_1$-$C_6CO_2^-$ anions chosen from formate, acetate, propionate, butyrate, hexanoate, maleate, fumarate, oxalate, lactate, and pyruvate. Sulfate anions, such as tosylate, mesylate, trifluoromethanesulfonate, trifluoroethane sulfonate, di-trifluoromethanesulfonyl amino can also be used as suitable anions in the imidazolium salt.

In certain examples, the quaternary ammonium salt is tetrabutylammonium chloride.

The amount of the quaternary ammonium salt can vary depending on the particular substrate. In certain examples, from about 0.5 to about 10 equivalents of the quaternary ammonium salt can be used per equivalent of the substrate. For example, from about 0.5 to about 9 equivalents, from about 0.5 to about 8 equivalents, from about 0.5 to about 7 equivalents, from about 0.5 to about 6 equivalents, from about 0.5 to about 5 equivalents, from about 0.5 to about 4 equivalents, from about 0.5 to about 3 equivalents, from about 0.5 to about 2 equivalents, from about 1 to about 10 equivalents, from about 1 to about 9 equivalents, from about 1 to about 8 equivalents, from about 1 to about 7 equivalents, from about 1 to about 6 equivalents, from about 1 to about 5 equivalents, from about 1 to about 4 equivalents, from about 1 to about 3 equivalents, from about 2 to about 10 equivalents, from about 2 to about 9 equivalents, from about 2 to about 8 equivalents, from about 2 to about 7 equivalents, from about 2 to about 6 equivalents, from about 2 to about 5 equivalents, from about 2 to about 4 equivalents, from about 2 to about 3 equivalents, from about 3 to about 10 equivalents, from about 3 to about 9 equivalents, from about 3 to about 8 equivalents, from about 3 to about 7 equivalents, from about 3 to about 6 equivalents, from about 3 to about 5 equivalents, from about 3 to about 4 equivalents, from about 4 to about 10 equivalents, from about 4 to about 9 equivalents, from about 4 to about 8 equivalents, from about 4 to about 7 equivalents, from about 4 to about 6 equivalents, from about 4 to about 5 equivalents, from about 5 to about 10 equivalents, from about 5 to about 9 equivalents, from about 5 to about 8 equivalents, from about 5 to about 7 equivalents, from about 5 to about 6 equivalents, from about 6 to about 10 equivalents, from about 6 to about 9 equivalents, from about 6 to about 8 equivalents, from about 6 to about 7 equivalents, from about 7 to about 10 equivalents, from about 7 to about 9 equivalents, from about 7 to about 8 equivalents, from about 8 to about 10 equivalents, from about 8 to about 9 equivalents, from about 9 to about 10 equivalents, or from about 0.5 to about 1 equivalent of the quaternary ammonium salt can be used per equivalent of the substrate.

Substrate

An advantage of the disclosed methods is that it can be effective at fluorinating a wide variety of substrates. It is particularly well suited for fluorinating aryl and heteroaryl substrates. In particular examples of the disclosed methods, the substrate can have Formula IA or IB:

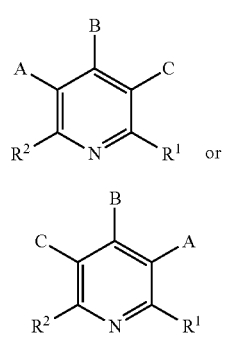

wherein
A is Cl, Br, SO$_2$R$^3$, or NO$_2$;
B is H, Cl, Br, SO$_2$R$^3$, or NO$_2$;
C is H, Cl, Br, SO$_2$R$^3$, or NO$_2$;
R$^1$ is H, CN, or CO$_2$R$^3$, wherein each R$^3$ is, independent of any other, optionally substituted C$_1$-C$_{12}$ alkyl, C$_2$-C$_{12}$ alkenyl, C$_2$-C$_{12}$ alkynyl, heterocycloalkyl, heteroaryl, cycloalkyl, or aryl; and
R$^2$ is H, substituted or unsubstituted aryl, or substituted or unsubstituted heteroaryl. The resulting fluorinated product can have Formula IIA or IIB

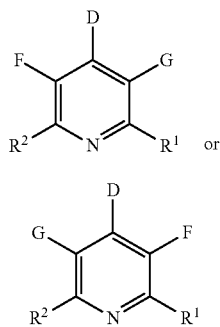

wherein D is B, as is defined above, or F; and G is B, as is defined above, or F.

The disclosed methods can be selective in that the competing product, a difluorinated or a para-fluorinated product, is present in an amount less than the amount of the product of Formula IIA or IIB. For example, the amount of bisfluorinated or a para-fluorinated product is less than the amount of the product of Formula IIA or IIB when D is B and G is B, as defined above.

Solvents

Solvents can also be used in the disclosed methods. Solvents can be added to the substrate, the KF, the quaternary ammonium salt, or any combination of these. Suitable solvents can be polar aprotic solvents. In certain examples, the solvent can be one or more of dimethylformamide (DMF), dimethylacetamide (DMAc), tetrahydrofuran (THF), sulfolane, and deuterated analogs thereof. In particular examples, the solvent can be acetonitrile or a deuterated analog thereof. In other examples, the solvent can be dimethylsulfoxide (DMSO) or a deuterated analog thereof. Any of these solvents alone or in combination with others solvents can be used in the methods disclosed herein.

If used in the disclosed methods, the amount of solvent can vary depending on the particular substrate. In certain examples, from about 0.5 to about 5 equivalents of the solvent can be used per equivalent of the substrate. For example, from about 0.5 to about 4.5 equivalents, from about 0.5 to about 4 equivalents, from about 0.5 to about 3.5 equivalents, from about 0.5 to about 3 equivalents, from about 0.5 to about 2.5 equivalents, from about 0.5 to about 2 equivalents, from about 0.5 to about 1.5 equivalents, from about 0.5 to about 1 equivalents, from about 1 to about 5 equivalents, from about 1 to about 4.5 equivalents, from about 1 to about 4 equivalents, from about 1 to about 3.5 equivalents, from about 1 to about 3 equivalents, from about 1 to about 2.5 equivalents, from about 1 to about 2 equivalents, from about 1 to about 1.5 equivalents, from about 1.5 to about 5 equivalents, from about 1.5 to about 4.5 equivalents, from about 1.5 to about 4 equivalents, from about 1.5 to about 3.5 equivalents, from about 1.5 to about 3 equivalents, from about 1.5 to about 2.5 equivalents, from about 1.5 to about 2 equivalents, from about 2 to about 5 equivalents, from about 2 to about 4.5 equivalents, from about 2 to about 4 equivalents, from about 2 to about 3.5 equivalents, from about 2 to about 3 equivalents, from about 2 to about 2.5 equivalents, from about 2.5 to about 5 equivalents, from about 2.5 to about 4.5 equivalents, from about 2.5 to about 4 equivalents, from about 2.5 to about 3.5 equivalents, from about 2.5 to about 3 equivalents, from about 3 to about 5 equivalents, from about 3 to about 4.5 equivalents, from about 3 to about 4 equivalents, from about 3 to about 3.5 equivalents, from about 3.5 to about 5 equivalents, from about 3.5 to about 4.5 equivalents, from about 3.5 to about 4.0 equivalents, from about 4 to about 5 equivalents, from about 4 to about 4.5 equivalents, or from about 4.5 to about 5 equivalents of the solvent can be used per equivalent of the substrate.

In specific examples of the disclosed methods, a fluorinated heteroaryl substrate can be prepared by steps comprising mixing KF, one or more tetraalkylammonium salts, a solvent, and a substrate having Formula IA or IB:

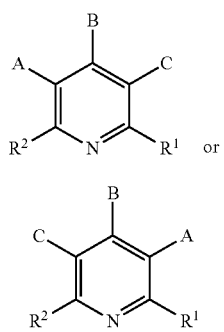

wherein
A is Cl, Br, $SO_2R^3$, or $NO_2$;
B is H, Cl, Br, $SO_2R^3$, or $NO_2$;
C is H, Cl, Br, $SO_2R^3$, or $NO_2$;
$R^1$ is H, CN, or $CO_2R^3$, wherein each $R^3$ is, independent of any other, optionally substituted $C_1$-$C_{12}$alkyl, $C_2$-$C_{12}$ alkenyl, $C_2$-$C_{12}$ alkynyl, heterocycloalkyl, heteroaryl, cycloalkyl, or aryl; and
$R^2$ is H, substituted or unsubstituted aryl, or substituted or unsubstituted heteroaryl. A tetraalkylammonium salt with a tetraalkylammonium cation having the formula) $^+N(R^{20})(R^{21})(R^{22})(R^{23})$, wherein $R^{20}$-$R^{23}$ are, independent of one another, methyl, ethyl, propyl, isopropyl, butyl, sec-butyl, isobutyl, pentyl, isopentyl, hexyl, 2-ethylbutyl, or 2-methylpentyl; and an anion chosen from $Cl^-$, $Br^-$, $C_1$-$C_6CO_2^-$, $OH^-$, $I^-$, $CN^-$, $SCN^-$, $OCN^-$, $CNO^-$, $N_3^-$, $CO_3^{2-}$, $HCO_3^-$, $HS^-$, $NO_2^-$, $NO_3^-$, $SO_4^{2-}$, $PO_4^{3-}$, $ClO^-$, $ClO_2^-$, $ClO_3^-$, $ClO_4^-$, $CF_3CO_2^-$, $CF_3SO_3^-$, and $C_6H_5CO_2^-$ can be used in the method.

The resulting fluorinated product can have Formula IIA or IIB

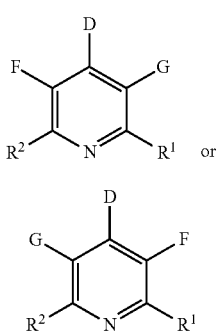

wherein D is B, as is defined above, or F; and G is B, as is defined above, or F.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

All reaction materials/solvents were weighed out in a glovebox under nitrogen ($N_2$) atmosphere unless stated otherwise. All substrates/solvents were dried before use. Yields were determined by nuclear magnetic resonance (NMR) spectroscopy using trifluorotoluene (10 microliters per reaction (μL/rxn)) as an internal standard. Yields for DS-1/DS-2 were determined by gas chromatography (GC) using 2-phenylpyridine as an internal standard (20 μL/rxn) and a calibration curve. NMR spectra were obtained on a Varian 500 (470.56 MHz for $^{19}$F) or Varian MR400 (376 MHz for $^{19}$F) spectrometer. Gas chromatography was carried out on a Shimadzu 17A using a Restek Rtx-5 (Crossbond 5% diphenyl-95% dimethyl polysiloxane; 15 meters (m), 0.25 millimeter (mm) ID, 0.25 micron (μm) df (film thickness)) column.

Isopropyl 5,6-dichloropicolinate

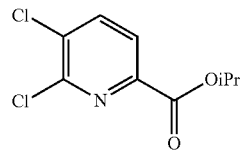

A four-neck 500 milliliter (mL) round bottomed flask was fitted with a thermocouple/J-KEM controller, mechanical stirrer, condenser that vented to a knock-out pot then to a 12% sodium hydroxide (NaOH) scrubber and a stopper. To the vessel was added concentrated sulfuric acid ($H_2SO_4$; 27.0 grams (g), 0.28 moles (mol)) and sulfolane (28.9 g). This mixture was warmed to 130° C. and then the solid trichloromethyl-pyridine (70.2 g, 0.26 mol) was added in portions over ca. 1 hour (h). Vigorous degassing to the caustic trap was observed. After the addition was complete, the mixture was stirred at 130° C. for 2 h and then allowed to cool to room temperature with stirring overnight resulting in a thick taffy. The mixture was warmed to 70° C., and a sample was taken for high performance liquid chromatography (HPLC) analysis which indicated a very clean conversion to the corresponding carboxylic acid. To the pot at 70° C. was carefully added isopropyl alcohol (IPA; 83.2 g, 1.39 mol) in portions over about 45 minutes (min) Initially there was vigorous degassing to the NaOH/caustic trap. After the addition was complete, the clear brown solution was stirred at 70° C. for 1 h. The 70° C. solution was added to crushed ice (361 g) with swirling of the flask. At the end of the addition, there was very little ice in the slurry. The slurry was cooled in the refrigerator for 1 h, and the solid was collected via filtration. The cake was washed with IPA/water (31 g/31 g) and then water (65 g). The material was allowed to air dry in a hood to a constant weight providing the product as a light beige solid (55 g, ca. 89%): HPLC purity was 98.5%; EIMS (70 eV) m/z 235, 233 (M+, 1%, 2%), 220, 218, 194, 192, 176, 174, 149, 147 (100%); $^1$H NMR (400 MHz, CDCl$_3$) 7.98, 7.91 (ABq, J=8.0 Hz, 2H), 5.30 (m, 1H), 1.41 (d, J=4.0 Hz, 6H).

Isopropyl 5-chloro-6-phenylpicolinate (DS-2)

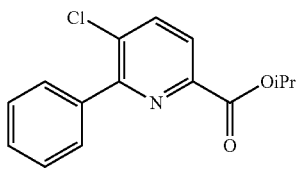 [SMILES: CC(C)OC(=O)c1ccc(Cl)c(-c2ccccc2)n1]

In a 500 mL three-neck round bottomed flask equipped with a mechanical over-head stirrer was charged potassium fluoride dihydrate (KF.2H$_2$O; 18.1 g, 192.6 millimoles (mmol)), tap water (70 mL), and acetonitrile (280 mL). The mixture was stirred until all the solids dissolved. To this biphasic mixture was added phenylboronic acid (9.39 g, 77.1 mmol), and then isopropyl 5,6-dichloropicolinate (15.0 g, 64.2 mmol). The resultant suspension was sparged with N$_2$ gas for 15 min and then bis(triphenyl-phosphine)palladium(II) dichloride (1.13 g, 1.61 mmol) was added. The bright yellow suspension was sparged with N$_2$ for another 15 min, and then the mixture was heated to 65° C. After stirring the mixture for 6 h, the reaction was deemed complete by HPLC analysis. The heating mantle was removed, and the mixture was cooled to ambient temperature. The mixture was diluted with ethyl acetate (150 mL) and water (50 mL). The layers were separated, and to the organic layer was added silica gel (EMD silica gel 60; 48 g). The solvent was then removed by rotary evaporator. The product was purified by CombiFlash chromatography using hexanes/ethyl acetate as elution solvents (gradient conditions: hexanes/ethyl acetate 95/5 to 80/20 in 15 minutes) to afford a thick oil (15.63 g, 88%) after evaporation of the chromatography solvent. A crystalline spec was added, and the product was isolated as a cream-white waxy crystalline solid weighing (15.03 g, 85%) that was >99% pure as estimated by HPLC. A small amount of the thick oil from a previous experiment was scratched and cooled in a test tube with the eventual formation of a white solid. This solid was added to a solution of the oil (4 g) dissolved in IPA (15 mL). After scratching to induce crystallization, the thick mixture was cooled for 1 h in a refrigerator, filtered, and washed with cold IPA (3 mL) to give a white solid (3.30 g). The solid was air dried in a hood overnight to give a white solid (3.16 g): mp 43-45° C.; $^1$H NMR (400 MHz, CDCl$_3$) δ 7.97 (d, J=8.4 Hz, 1H), 7.88 (d, J=8.0 Hz, 1H), 7.80-7.77 (m, 2H), 7.49-7.44 (m, 3H), 5.31 (hept, J=6.4 Hz, 1H), 1.41 (d, J=6.4 Hz, 6H, CH$_3$); $^{13}$C NMR (100.6 MHz, CDCl$_3$) δ 163.9, 156.6, 146.7, 138.7, 137.4, 133.4, 129.6, 129.1, 128.0, 124.0, 69.7, 21.8; EIMS (70 eV) m/z Calcd. for C$_{15}$H$_{14}$ClNO$_3$: (M+) 275.7. Found: 275 (M+), 216 [(M+-OiPr)], 189 [(M+-CO$_2$iPr)].

Comparative Example 1

Fluorination of isopropyl 5-chloro-6-phenylpicolinate with CsF

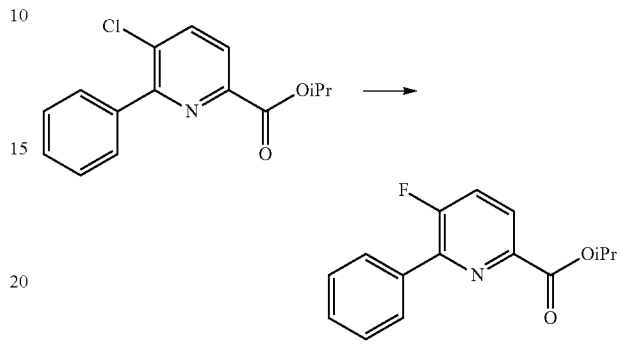

The reaction was carried out in a glove box. To a glass jar equipped with a stir bar was added isopropyl 5-chloro-6-phenylpicolinate (DS-2; 1.103 g, 4 mmol), cesium fluoride (CsF; 1.215 g, 8 mmol) and dimethyl sulfoxide (DMSO, anhydrous grade; 8.5 g). The mixture was heated to 120° C. on a heating block for 19 h. A sample was taken and analyzed by GC which indicated this reaction was complete. The mixture was cooled to room temperature. The salts were removed by filtration and washed with a little DMSO. The mixture was poured into a separatory funnel with water and extracted with ethyl acetate. The organic phase was then washed with water and dried over anhydrous magnesium sulfate (MgSO$_4$). The solvent was removed with a rotary evaporator. The concentrated crude product was purified using column chromatography (silica gel, MP SiliTech 32-63D) with an ethyl acetate/hexanes mixture (1/5) as eluent to give 0the desired product as a pale yellow liquid (0.86 g, 81%, ~100% GC purity, 98% LC purity): $^1$H NMR (400 MHz, CDCl$_3$) δ 8.06 (m, 3H), 7.56 (dd, J=10.4, 8.5 Hz, 1H), 7.53-7.41 (m, 3H), 5.32 (hept, J=6.3 Hz, 1H), 1.43 (d, J=6.3 Hz, 6H); $^{13}$C NMR (101 MHz, CDCl$_3$) δ 163.78 (s), 160.42 (s), 157.77 (s), 146.28 (d, J=11.7 Hz), 144.49 (d, J=4.8 Hz), 134.58 (d, J=5.6 Hz), 129.66 (s), 129.08 (s), 129.03 (s), 128.49 (s), 125.32 (d, J=5.5 Hz), 124.55 (d, J=21.4 Hz), 69.58 (s), 21.90 (s); $^{19}$F NMR (376 MHz, CDCl$_3$) δ −117.82 (s); EIMS (70 eV) m/z 259 (8.3%), 174 (12.5%), 173 (100%), 172 (35.4%), 145 (9.4%). The in-pot yield was 83% (GC) as determined by using purified isopropyl 5-fluoro-6-phenylpicolinate as a standard and dipropyl phthalate as a reference.

Comparative Example 2

Fluorination of isopropyl 5-chloro-6-phenylpicolinate with KF

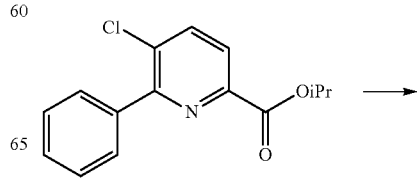

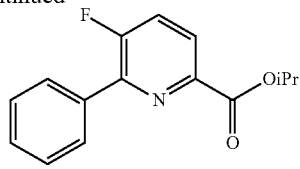

The reaction was carried out in a glove box. To a glass jar equipped with a stir bar was added isopropyl 5-chloro-6-phenylpicolinate (DS-2; 0.551 g, 2 mmol), 18-crown-6 (0.106 g, 0.4 mmol), KF (0.232 g, 4 mmol) and DMSO (anhydrous grade, 4 g). The fluorination without 18-crown-6 was set up on the same scale in parallel. The mixtures were heated to 120° C. on a heating block for 23 h. A sample was taken and analyzed by LC and/or GC. LC showed that the reaction with 18-crown-6 was not complete with 9% of product (isopropyl 5-fluoro-6-phenylpicolinate) and 91% of starting material (isopropyl 5-chloro-6-phenylpicolinate). GC showed that the reaction without 18-crown-6 was not complete with 5% of product (isopropyl 5-fluoro-6-phenylpicolinate) and 95% of starting material (isopropyl 5-chloro-6-phenylpicolinate).

Comparative Examples 3 and 4

Fluorination of ethyl 5-chloro-6-phenylpicolinate

Analogous reactions to Comparative Examples 1 and 2 were performed except the substrate isopropyl 5-chloro-6-phenylpicolinate (DS-2) was replaced with ethyl 5-chloro-6-phenylpicolinate (DS-1). Results for the comparative examples 1-4 are shown in FIG. 1.

Increased reactivity of DS-2 over DS-1 was observed. Reactions with CsF (2 equivalents (equiv)) proceeded to 80% yield of the desired fluorinated pyridine, while KF (2 equiv) did not exceed 10% yield (FIG. 1).

Example 5

Fluorination Using Tetrabutylammonium Chloride and KF

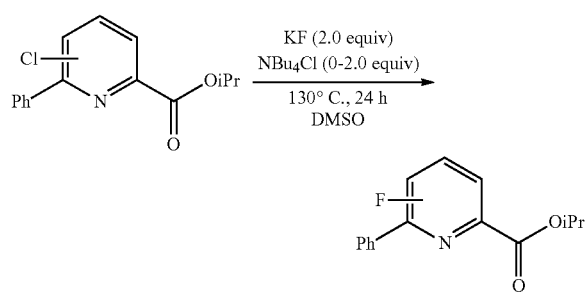

With the baseline fluorinations confirmed for CsF and KF, the efficient fluorination of DS-2 was demonstrated using a combination of KF and tetrabutylammonium chloride (NBu$_4$Cl). Specifically, DS-2 (50 mg), and all other solids (metal fluorides/quaternary ammonium salts/additives) were weighed into a 4 mL vial equipped with a micro stirbar. DMSO (0.5 mL) was added, and the vial was sealed with a Teflon-lined screwcap. The reaction vial was removed from the N$_2$ drybox and placed on an IKA® heating/stirring plate with temperature probe, equipped with an aluminum heating block. The reaction was heated/stirred at the specified temperature (generally 130° C. or 150° C.) for the given amount of time (generally 24 h). After the reaction was complete it was allowed to cool to room temperature, diluted with dichloromethane (DCM), and internal standard(s) were added. Yields were determined by $^{19}$F NMR spectroscopy and GC.

Figure 2:
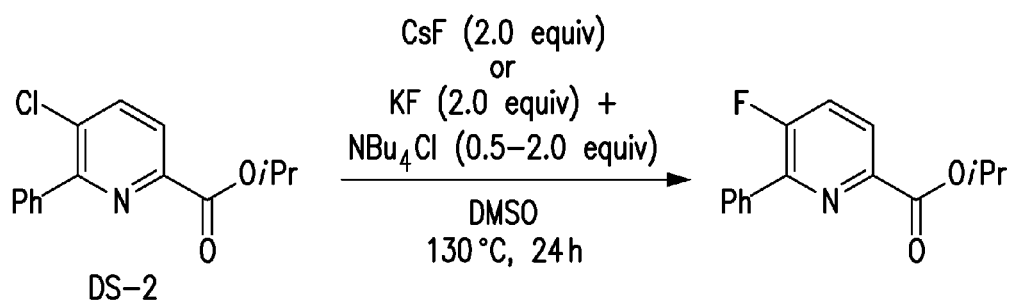
FIG. 2 contains a graph showing the fluorination yield of the reaction depicted above the graph (%) with isopropyl 5-chloro-6-phenylpicolinate (DS-2) using KF in the presence of tetrabutylammonium chloride, as compared to CsF.
Figure 2:
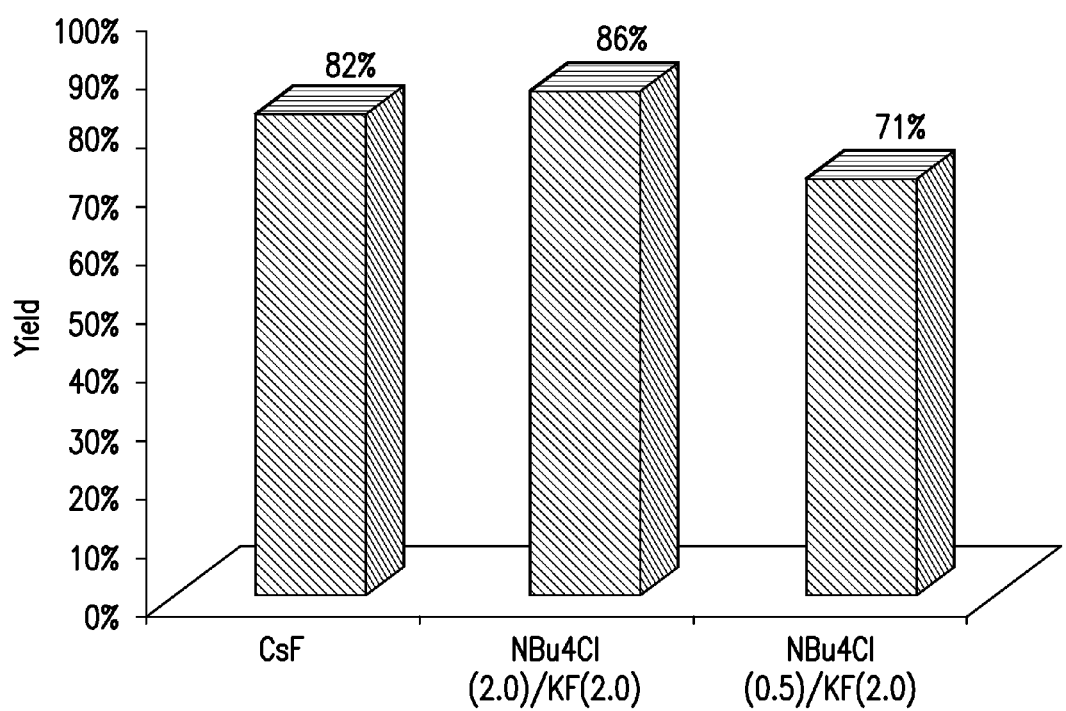

It was found that this method is comparable to the method of employing cesium fluoride, which is significantly more expensive than potassium fluoride. High yields were achieved at 130° C. with stoichiometric (2.0 equiv, 86% yield) as well as substoichiometric (0.5 equiv, 71% yield) amounts of NBu$_4$Cl (FIG. 2).

Example 6

Fluorination Using Various Tetrabutylammonium Salts and KF

Figure 3:
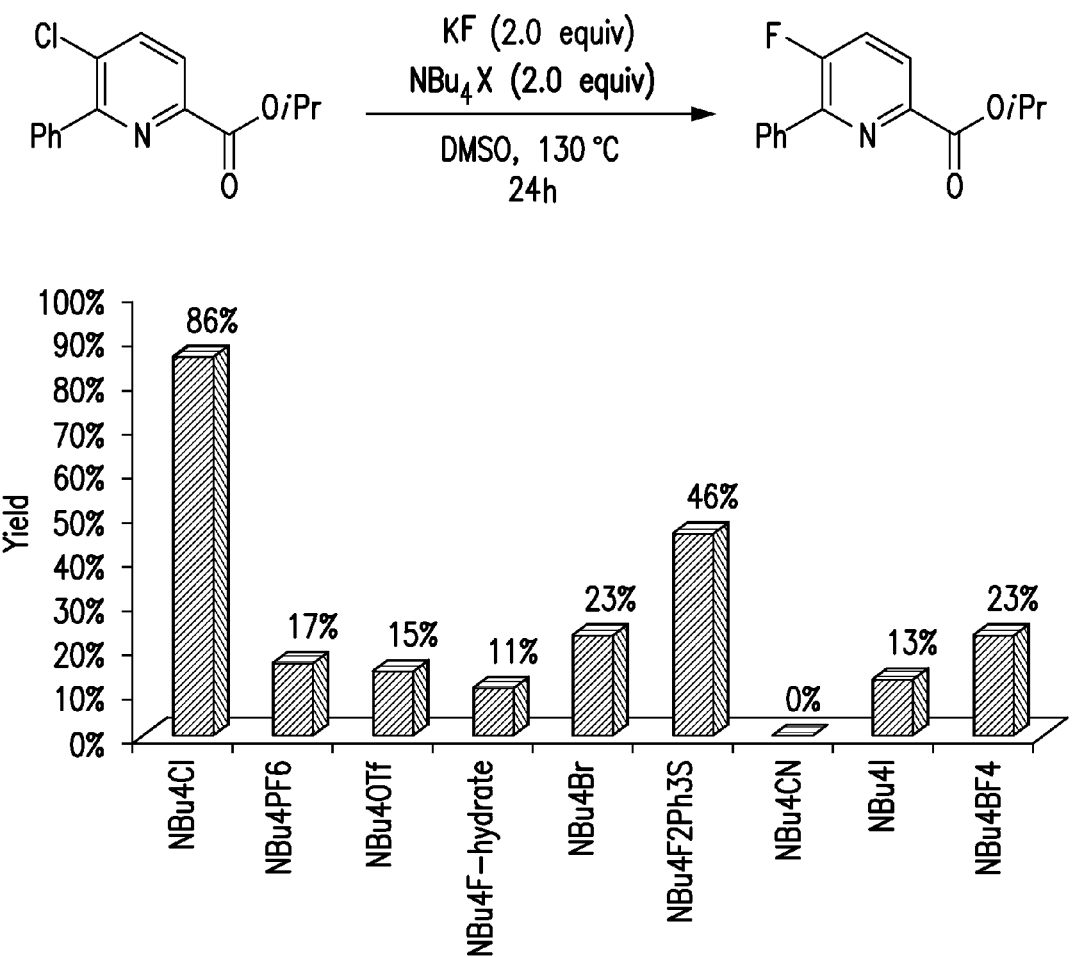
FIG. 3 contains a graph showing the fluorination yield of the reaction depicted above the graph (%) with isopropyl 5-chloro-6-phenylpicolinate (DS-2) using KF in the presence of different tetrabutylammonium salts.

In a procedure similar to Example 5, different tetrabutylammonium salts (2.0 equiv) with KF (2.0 equiv) were screened to meet or exceed the reactivity of DS-2 with CsF. Tetrabutylammonium chloride (NBu$_4$Cl) provided the best results relative to all of the tetrabutylammonium salts screened (FIG. 3).

Example 7

Fluorination Using Various Equivalents of Tetrabutylammonium Chloride and KF

Figure 4:
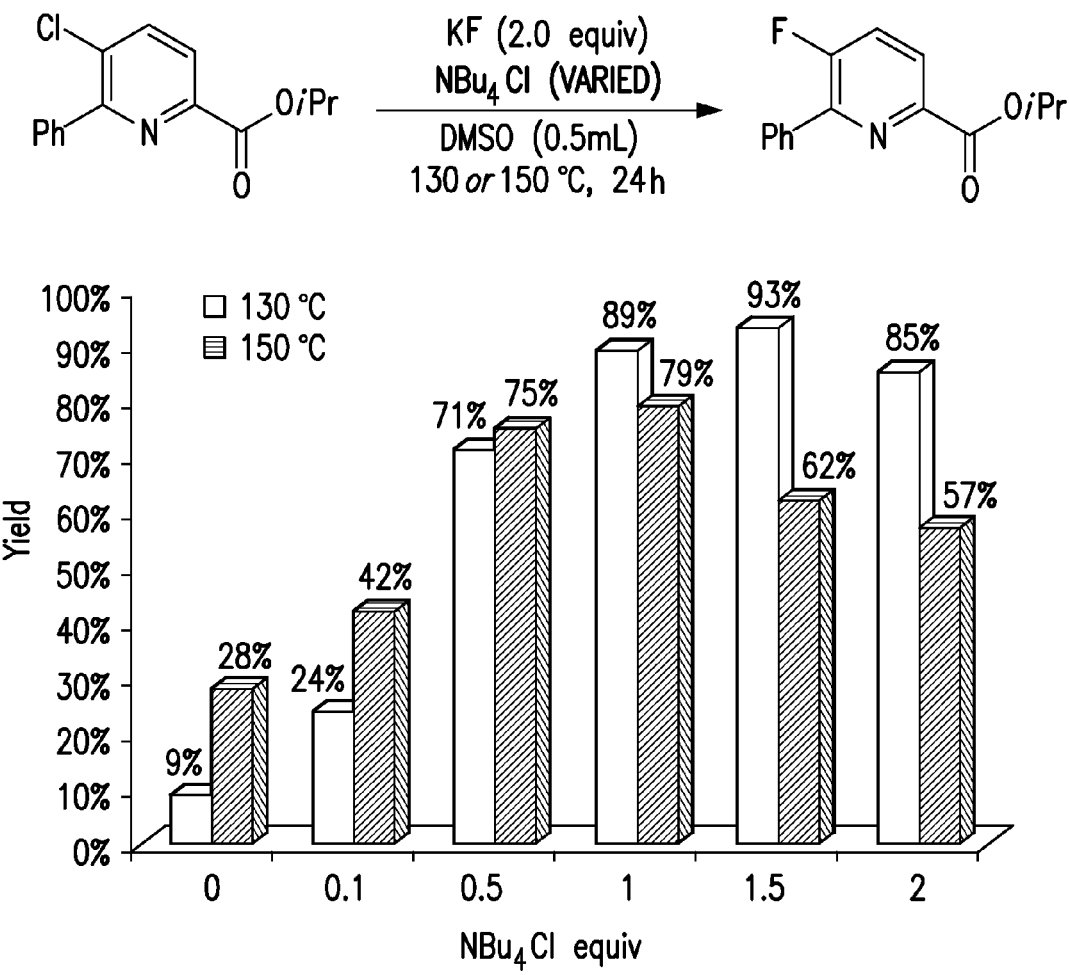
FIG. 4 contains a graph showing the fluorination yield of the reaction depicted above the graph (%) with isopropyl 5-chloro-6-phenylpicolinate (DS-2) using KF in the presence of different amounts of tetrabutylammonium chloride.

The equivalents of NBu$_4$Cl were next evaluated. As shown in FIG. 2, the yield of the desired fluorinated pyridine diminished as the equivalents of NBu$_4$Cl were lowered. It was found, however, that greater than 50% yield could be achieved with only 0.5 equiv of NBu$_4$Cl together with KF (2.0 equiv) in DMSO at 130° C. (FIG. 4).

Example 8

Fluorination Using Various Tetramethylammonium Salts and KF

Figure 5:
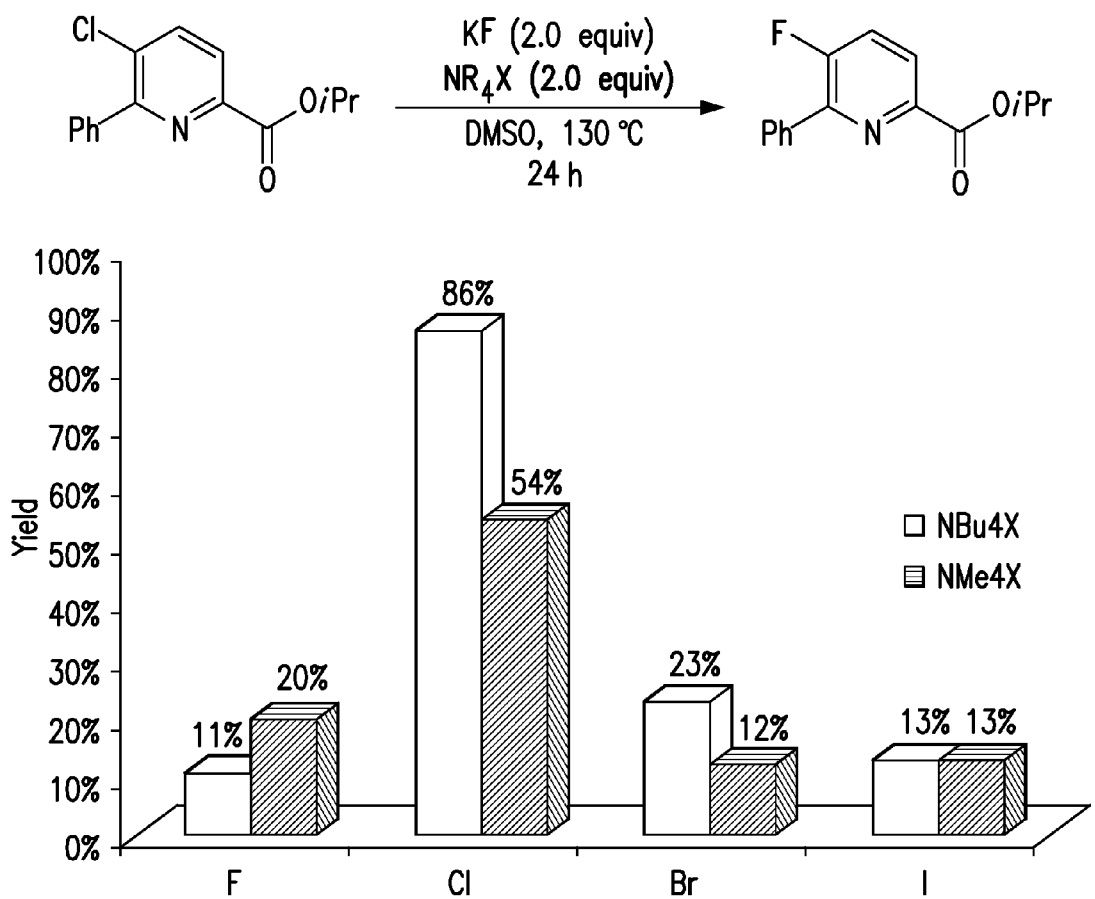
FIG. 5 contains a graph showing the fluorination yield of the reaction depicted above the graph (%) with isopropyl 5-chloro-6-phenylpicolinate (DS-2) using KF in the presence of different quaternary ammonium salts.

Procedures analogous to Example 6 above were performed except tetramethylammonium salts were used. The chloride salt was again found to be superior when the tetramethylammonium salts were examined for the fluorination of DS-2. Looking at NMe$_4$X (X=F, Cl, Br, I), tetramethylammonium chloride (NMe$_4$Cl) showed the highest activity; however, it only produced 54% yield at 2.0 equiv loading. The other halogen counteranions failed to give fluorination in yields greater than 20% (FIG. 5).

Example 9

Fluorination Using Various Solvents

Figure 6A:
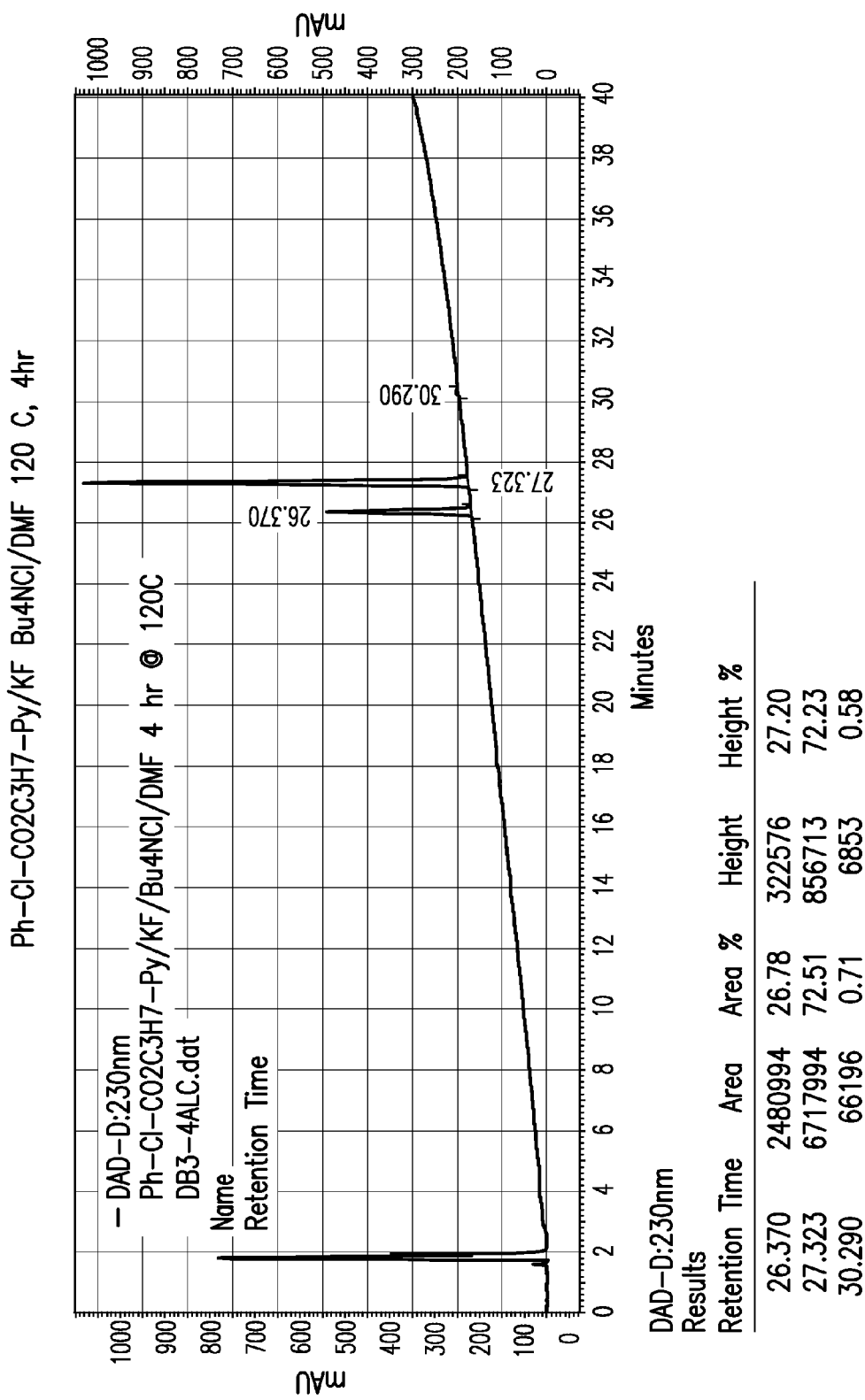
FIG. 6A is a liquid chromatography (LC) trace of the reaction mixture of the fluorination of isopropyl 5-chloro-6-phenylpicolinate (DS-2) using KF and tetrabutylammonium chloride in various solvents taken at 4 h
Figure 6B:
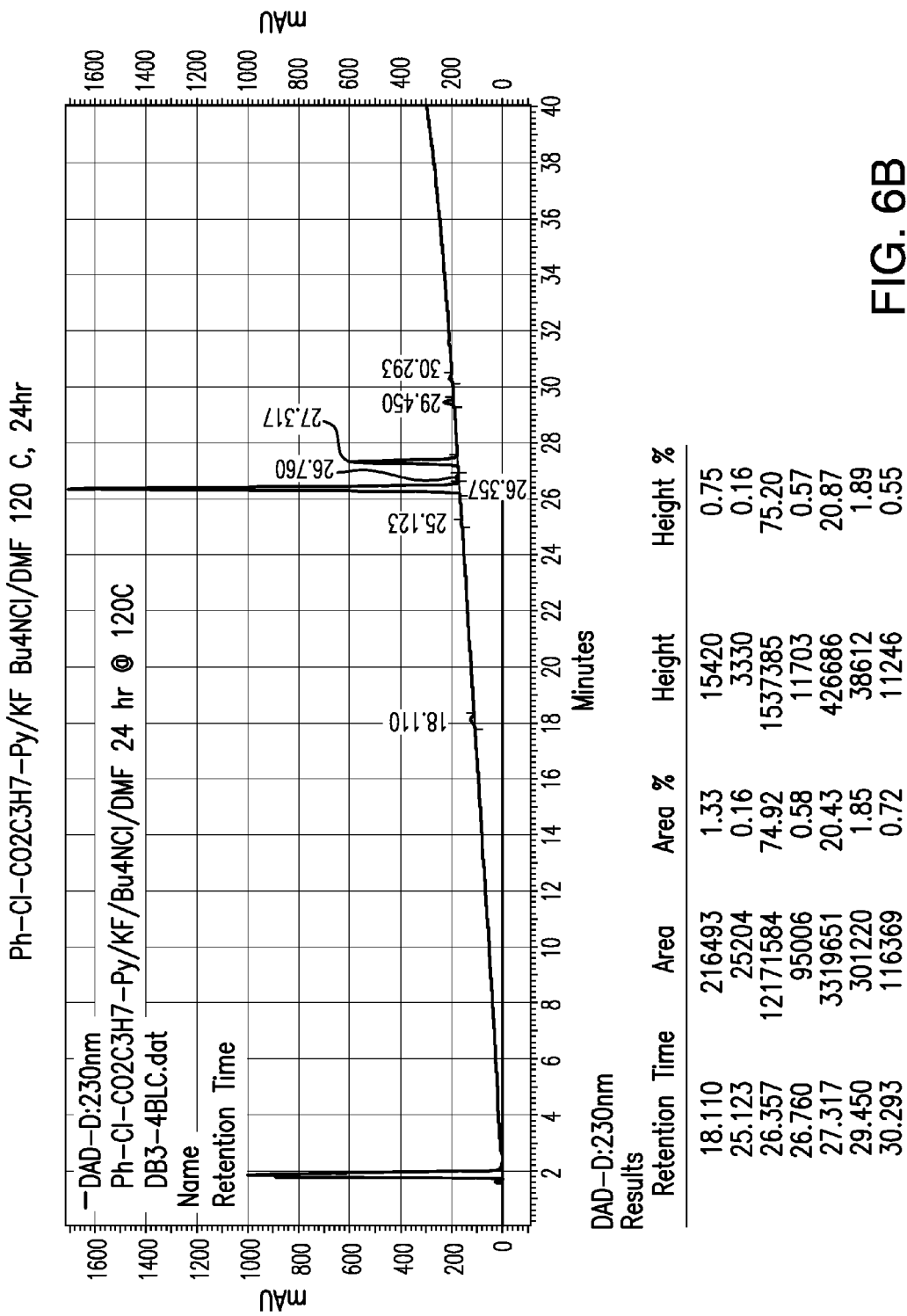
FIG. 6B is a LC trace of the reaction mixture take 24.

Procedures similar to Example 5 were performed except that different solvents were used instead of DMSO. For example, to a 30 mL glass vial with screwcap and a magnetic stir bar were charged isopropyl 5-chloro-6-phenylpicolinate (DS-2; ~280 mg, 1.02 mmol), KF (~118 mg, 2.03 mmol), and dry tetrabutylammonium chloride (~564 mg, 2.03 mmol) followed by DMF (~3.3 g, 45.15 mmol). The mixture was heated to 120° C. and stirred for a period of time. At about 4 h, LC analysis of the reaction mixture indicated 72.5% (relative area) of starting DS-2 and 26.8% (relative area) of desired isopropyl 5-fluoro-6-phenylpicolinate (see FIG. 6A). After 24 h, LC analysis of the reaction mixture indicated 20.4% (relative area) of starting DS-2 and 74.9% (relative area) of desired isopropyl 5-fluoro-6-phenylpicolinate (see FIG. 6B). The reaction mixture was filtered through a filter disc, and the cake was rinsed with fresh acetonitrile to afford a light yellow solution (5.4 g). LC analysis (using dipropyl phthalate as the internal standard) of the isolated mixture indicated a 78% in-pot yield of isopropyl 5-fluoro-6-phenylpicolinate.

Figure 7:
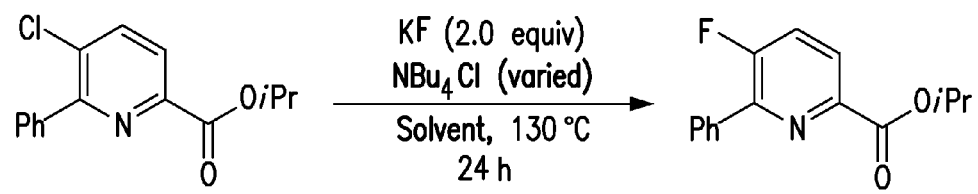
FIG. 7 contains a graph showing the fluorination yield of the reaction depicted above the graph (%) with isopropyl 5-chloro-6-phenylpicolinate (DS-2) using KF in the presence tetrabutylammonium chloride in different solvents.
Figure 7:
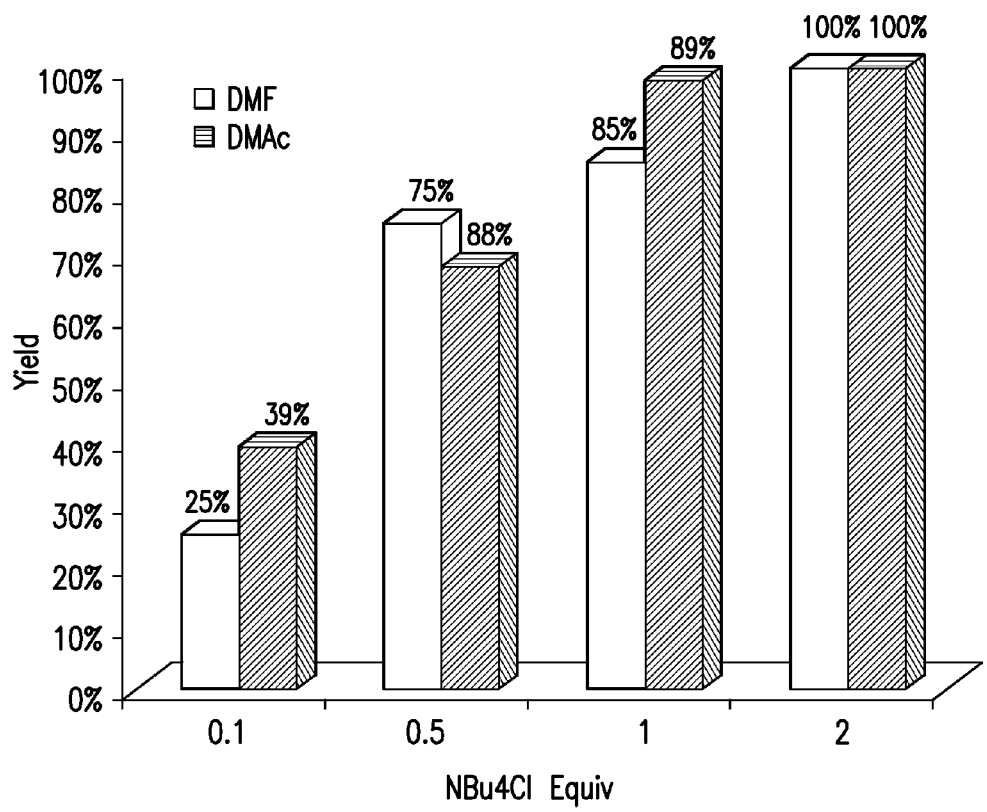

It was thus found that other polar aprotic solvents such as dimethylformamide (DMF) and dimethylacetamide (DMAc) were quite efficient at affecting the desired fluorination with tetrabutylammonium chloride/KF (2.0 equiv each) at 130° C. Both DMF and DMAc provided full conversion of DS-2 to the desired fluorinated product within 24 h (FIG. 7).

In all of the quaternary ammonium salts evaluated, those with chloride anion outperformed all others. Additionally, three salts, tetrabutylammonium chloride, tetraphenylphosphonium chloride, and bis(triphenylphosphoranylidene) ammonium chloride, provided >75% yield at 2.0 equiv and 130° C. Screens at 0.1 equiv of the salts did not produce yields >25% at 130° C. in any case. When the temperature was increased, the yields increased at low loadings (~40% at 0.1 equiv salt loading); however, diminished yields were observed for all three salts at loadings between 1.0-2.0 equiv.

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A method of preparing a fluorinated product, comprising: combining potassium fluoride, one or more quaternary ammonium salts, and a substrate, to thereby provide the fluorinated product, wherein the substrate has Formula IA or IB:

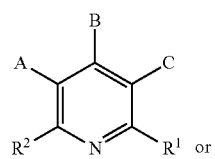

IA

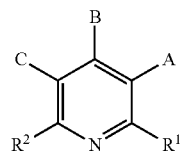

IB wherein
A is Cl, Br, $SO_2R^3$, or $NO_2$;
B is H, Cl, Br, $SO_2R^3$, or $NO_2$;
C is H, Cl, Br, $SO_2R^3$, or $NO_2$;
$R^1$ is H, CN, or $CO_2R^3$, wherein each $R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and
$R^2$ is H, substituted or unsubstituted aryl, or substituted or unsubstituted heteroaryl;
and wherein the fluorinated product has Formula IIA or IIB:

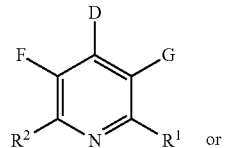

IIA

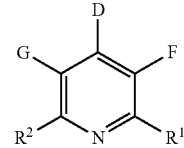

IIB wherein D is B or F; and G is B or F.

2. The method of claim 1, wherein the quaternary ammonium salt comprises a tetraalkyl ammonium cation having Formula $^+N(R^{20})(R^{21})(R^{22})(R^{23})$, wherein $R^{20}$-$R^{23}$ are, independent of one another, substituted or unsubstituted $C_1$-$C_{40}$ alkyl, substituted or unsubstituted $C_2$-$C_{40}$ alkenyl, substituted or unsubstituted $C_2$-$C_{40}$ alkynyl, substituted or unsubstituted $C_3$-$C_8$ cycloalkyl, or substituted or unsubstituted $C_3$-$C_8$ cycloalkenyl.

3. The method of claim 2, wherein each $R^{20}$-$R^{23}$ are, independent of one another, methyl, ethyl, propyl, isopropyl, butyl, sec-butyl, isobutyl, pentyl, isopentyl, hexyl, 2-ethylbutyl, or 2-methylpentyl.

4. The method of claim 1, wherein the quaternary ammonium salt comprises a trialkyl benzyl ammonium cation having Formula III:

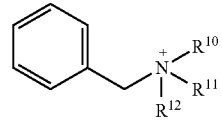

III wherein each $R^{10}$-$R^{12}$ are, independent of one another, substituted or unsubstituted $C_1$-$C_{40}$ alkyl or substituted or unsubstituted $C_3$-$C_8$ cycloalkyl.

5. The method of claim 4, wherein $R^{10}$ is $C_{10}$-$C_{40}$ alkyl and $R^{11}$ and $R^{12}$ are, independent of one another, substituted or unsubstituted $C_1$-$C_6$ alkyl.

6. The method of claim 1, wherein the quaternary ammonium salt comprises an anion chosen from $Cl^-$, $Br^-$, and $C_1$-$C_6CO_2^-$.

7. The method of claim 1, wherein the quaternary ammonium salt comprises an anion chosen from $OH^-$, $I^-$, $CN^-$, $SCN^-$, $OCN^-$, $CNO^-$, $N_3^-$, $CO_3^{2-}$, $HCO_3^-$, $HS^-$, $NO_2^-$, $NO_3^-$, $SO_4^{2-}$, $PO_4^{3-}$, $PF_6^-$, $ClO^-$, $ClO_2^-$, $ClO_3^-$, $ClO_4^-$, $CF_3CO_2^-$, $CF_3SO_3^-$, $BF_4^-$, and $C_6H_5CO_2^-$.

8. The method of claim 1, wherein the potassium fluoride and substrate are combined, followed by the addition of the quaternary ammonium salt.

9. The method of claim 1, wherein the quaternary ammonium salt and substrate are combined, followed by the addition of potassium fluoride.

10. The method of claim 1, further comprising the addition of a solvent.

11. The method of claim 10, wherein the solvent comprises one or more of dimethylformamide, dimethylacetamide, tetrahydrofuran, sulfolane, or deuterated analogs thereof.

12. The method of claim 10, wherein the solvent comprises acetonitrile or a deuterated analog thereof.

13. The method of claim 10, wherein the solvent comprises dimethylsulfoxide or a deuterated analog thereof.

14. The method of claim 1, further comprising heating the combination of potassium fluoride, the quaternary ammonium salt, and the substrate to from about 75 to about 200° C.

15. The method of claim 1, wherein from about 0.5 to about 10 equivalents of the quaternary ammonium salt is used per equivalent of the substrate.

16. The method of claim 1, wherein from about 0.5 to about 10 equivalents of potassium fluoride is used per equivalent of the substrate.

17. The method of claim 1, wherein the quaternary ammonium salt is tetrabutylammonium chloride.

18. The method of claim 1, wherein a difluorinated or a para-fluorinated product is present in an amount less than the amount of Formula IIA or IIB.

19. A method of preparing a fluorinated heteroaryl substrate, comprising: mixing potassium fluoride, one or more tetraalkylammonium salts, a solvent, and a substrate having Formula IA or IB:

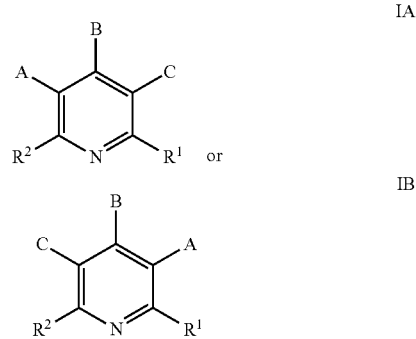

wherein
A is Cl, Br, $SO_2R^3$, or $NO_2$;
B is H, Cl, Br, $SO_2R^3$, or $NO_2$;
C is H, Cl, Br, $SO_2R^3$, or $NO_2$;
$R^1$ is H, CN, or $CO_2R^3$, wherein each $R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and
$R^2$ is H, substituted or unsubstituted aryl, or substituted or unsubstituted heteroaryl.

20. The method of claim 19, wherein the tetraalkyl ammonium salt is tetrabutylammonium chloride.

* * * * *

UNITED STATES PATENT AND TRADEMARK OFFICE
CERTIFICATE OF CORRECTION

PATENT NO. : 9,493,415 B2  
APPLICATION NO. : 14/539696  
DATED : November 15, 2016  
INVENTOR(S) : Allen et al.

Page 1 of 1

It is certified that error appears in the above-identified patent and that said Letters Patent is hereby corrected as shown below:

On the Title page

Right Column, at item (73), the Assignee should also include --The Regents of the University of Michigan, Ann Arbor MI (US)--

Signed and Sealed this  
Thirteenth Day of June, 2017

Joseph Matal  
*Performing the Functions and Duties of the*  
*Under Secretary of Commerce for Intellectual Property and*  
*Director of the United States Patent and Trademark Office*